United States Patent
Hansen et al.

(10) Patent No.: US 8,632,508 B2
(45) Date of Patent: Jan. 21, 2014

(54) MECHANISM FOR INJECTION DEVICE

(75) Inventors: Torben Stroem Hansen, Copenhagen (DK); Matias Melander, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 650 days.

(21) Appl. No.: 12/302,637

(22) PCT Filed: May 7, 2007

(86) PCT No.: PCT/EP2007/054395
§ 371 (c)(1),
(2), (4) Date: Jan. 5, 2009

(87) PCT Pub. No.: WO2007/137930
PCT Pub. Date: Dec. 6, 2007

(65) Prior Publication Data
US 2010/0241066 A1 Sep. 23, 2010

Related U.S. Application Data

(60) Provisional application No. 60/809,550, filed on May 31, 2006.

(30) Foreign Application Priority Data

May 29, 2006 (EP) .................................. 06114622

(51) Int. Cl.
*A61M 5/315* (2006.01)
(52) U.S. Cl.
USPC ............................................ 604/230; 604/68
(58) Field of Classification Search
USPC ............. 604/68–70, 134–136, 211, 229–230
See application file for complete search history.

(56) References Cited

U.S. PATENT DOCUMENTS

| | | | | |
|---|---|---|---|---|
| 5,253,785 | A | * | 10/1993 | Haber et al. ..................... 222/43 |
| 2002/0120235 | A1 | * | 8/2002 | Enggaard ...................... 604/135 |
| 2005/0277886 | A1 | | 12/2005 | Hommann et al. |
| 2006/0089593 | A1 | | 4/2006 | Landau et al. |
| 2006/0264830 | A1 | | 11/2006 | Hommann |

FOREIGN PATENT DOCUMENTS

| | | |
|---|---|---|
| EP | 834330 | 4/1998 |
| GB | 2414398 | 11/2005 |
| JP | 2001-187139 A | 7/2001 |
| JP | 2001-340456 A | 12/2001 |
| WO | WO99/40958 | 8/1999 |
| WO | WO2004/028598 | 4/2004 |
| WO | WO2005/044344 | 5/2005 |
| WO | WO 2006045526 A1 * | 5/2006 |

* cited by examiner

*Primary Examiner* — Jason Flick
*Assistant Examiner* — Melissa A Snyder
(74) *Attorney, Agent, or Firm* — Wesley A. Nicolas; Marc A. Began; Reza Green

(57) ABSTRACT

A pressurized injection device comprises a mechanical loading mechanism comprising a double set of rackets (17,18) and ball bearings/pins running in a curved track (20) which enables a resilient element (7) to be pre-stressed by—twisting the two outer house parts of the device relative to each other back and forth. When twisted in one direction one set of rackets (17) engages the teeth of the piston rod (9) connected to the resilient element and when twisted in the opposite direction, the other set of rackets (18) engages same piston rod. The resilient element is set off to engage a plunger of a container holding a drug to be injected by pressing the release button (1), which can be secured by a safety switch.

7 Claims, 3 Drawing Sheets

MECHANISM FOR INJECTION DEVICE

CROSS-REFERENCE TO RELATED APPLICATIONS

This application is a 35 U.S.C. §371 national stage application of International Patent Application PCT/EP2007/054395 (published as WO 2007/137930), filed May 7, 2007, which claimed priority of European Patent Application 061146221, filed May 29, 2006; this application further claims priority under 35 U.S.C. §119 of U.S. Provisional Application 60/809,550, filed May 31, 2006.

The invention relates to a mechanism for loading a pressurized injection device adapted for placement against the skin surface of a subject, for injecting a dose of drug to the subject. The mechanism of this invention gears down the force of the pressurizing spring to a low user loading force with a low friction mechanism and also makes it possible to load the device without changing the users grip on the device.

BACKGROUND OF THE INVENTION

Subcutaneous and intramuscular delivery of liquid drugs by injection is common in the medical arts. As some medications such as insulin must be given frequently by injection to an individual, easy performance of the injections is desirable.

Many patients dislike needle injections due to pain or fear for needles. Further, blood-borne pathogens, such as HIV and hepatitis, can be transmitted to health care workers by accidental needle-sticks. Also, the disposal of used needles is a growing concern. This disposal presents a problem to individuals other than healthcare workers. Children, for example, may find used needles in the garbage, putting them at risk of contracting infection. Discarded needles likewise pose a risk to waste disposal workers. This is at the moment a huge worldwide problem, (though partly overlooked as it mainly hits countries of low development) causing deaths counted in millions, In efforts to minimize the fears and risks associated with needle injections, several types of needle-free jet injectors have been developed. These devices penetrate the skin using a high velocity fluid jet and deliver medication into the tissue of a patient. In order to accomplish this, a force is exerted on the liquid medication. Jet injectors in general contain a fluid drug which has been transferred into a chamber having a small orifice at one end. A drive means, e.g. a ram, is accelerated using either a coil spring or a compressed gas energy source. The ram impacts a plunger which in turn creates a high pressure impulse within the chamber. This pressure impulse ejects the fluid medicament through the orifice at high velocity, piercing the skin. The energy source continues to apply a force to the plunger which quickly propels the drug through the opening in the skin, emptying the injection chamber in a fraction of a second. The drive means may be adapted to provide a two-stage injection, i.e. a first penetrating burst of drug at a high pressure followed by a subsequent delivery of the remaining amount of drug at a lower pressure. It shall be noted that the same principle of having a pressurized injection device can also be used for needle-injectors, in the case where it is desirable to enable an injection without a person having to press in the drug by her- or him-self when injecting. This can be the case if it is desirable to have a well known injection pressure and time, or if the user feels discomfort by having to perform the actual injection.

The energy impulse exerted on the pressurized injector in order to provide a sufficiently high-powered injection, especially when performing jet injections, is of a magnitude which require an energy source with a power level higher than is known from conventional manual injection devices. Systems that require a higher pressure or a certain level of automation often benefit from a build-in energy source such as a gas cartridge, pyrotechnical unit or a mechanical spring. The main advantage of using a mechanical spring is the ability of re-use whereas the e.g. gas operated systems require exchange of the gas unit or discarding of the whole device when it has been used. However, the pre-stressing of a spring requires a certain level of force provided by the user or some additional power such as a motor which again require either batteries or an external energy supply. To ensure handling simplicity, manual loading by the user is thus desirable.

There are several spring operated injection systems on the market addressing this problem. In most cases the spring is either loaded by a twisting operation or a separate device dedicated for the loading procedure. The devices that require a twisting operation by the user are in many cases (e.g. MHI 500 of the Medical House disclosed in EP 1332767 and Ltd. Medi-Jector Vision of Antares Pharma disclosed in U.S. Pat. No. 5,879,327) designed with a thread for the spring pre-stressing operation. Such a thread will impose a certain degree of mechanical loss depending on the friction of the thread interaction. This causes an unwanted additional effort by the user. Other known devices are described in US 2006089593 and EP 0834330, where only a single set of one-way fixation means are provided.

In view of the above, one of the objectives of the present invention is to provide a mechanism for loading a pressurized injection device which enables the device to be manually loaded.

It is a further objective of the present invention to provide a loading mechanism that ensures the injection device is reusable.

Yet a further objective is to provide a loading mechanism which is effective in extracting maximum gain from the loading force provided by the user through an efficient gearing and low friction.

A further objective is also to ensure ease of handling by the user.

A further objective of the present invention is to provide a simple loading mechanism for a pressurized injection device.

In the alternative, it is a further objective to provide a pressurized injection device with resemblance of a conventional pen type injector as regards function and configuration, in order to make the patient comfortable with the jet injection device and so that the injection device can easily be utilized by a non-professional user, e.g. a insulin requiring diabetic.

SUMMARY OF THE INVENTION

In the disclosure of the present invention, embodiments and aspects will be described which will address one or more of the above objectives or which will address objectives apparent from the below disclosure as well as from the description of exemplary embodiments.

In a first aspect, a pressurized injection device is provided comprising a container for holding a drug. The container has in the distal end means for injecting the drug, an orifice or a needle and in the proximal end a plunger adapted to enclose the drug and force the drug out of the container when an injection is performed. The injection device housing encloses a drive mechanism with means for loading, holding and letting off a resilient element. A trigger mechanism is holding the resilient element in its loaded position. When the release button is pushed, the resilient element is let off, and then pushes a piston rod towards the plunger, whereby the drug in expelled. A safety switch can be provided, so the resilient element is not let of unintended. The present invention is concerned with the loading mechanism of the resilient element and the rest of the injection device will therefore not be described in further detail.

The resilient member, which in one embodiment can be a mechanical spring, is pre-stressed to provide the injection pressure. To ensure ease of handling when manually loading the pressurised injection device, the mechanical loading mechanism according to this invention pre-stresses the spring in a number of cyclic steps, in one embodiment by the use of a low friction force transfer element, such as a set of ball bearings rolling in a curved track or a set of pins. The outer shell of the house is divided in a proximal and a distal part adapted to be gripped by the user, each part of the device in each hand. The two parts are twisted at an angle corresponding to the angle of the curved track back and forth until the piston rod of the device reaches its endpoint in the fully loaded state. The rolling of the bearings provides a significantly higher efficiency than a thread system, since a thread system has a relatively large contact-surface between the two twisted parts, imposing a frictional loss to the system. If pins are used instead of bearings, still only a relatively small area is in contact with the track, making it easy to reduce the frictional losses by coating the pins with a low friction material. This can be achieved with a coated thread as well, but this requires a much more delicate and expensive manufacturing process. A further advantage of the described invention is that the user can load the device without change of grip, since it integrates a double set of ratchets holding the piston rod in position while the user reverse the dial in between loading operations.

In stead of a curved track and bearing or pins connecting the two outer shell parts of the housing, in another embodiment of the invention the shell parts them selves can have corresponding curved end edges engaging each other either directly or with a friction limiting member such as a ball or a roller. Likewise, the two outer shell parts can be connected via a linkage performing the needed axial movement of the two parts relative to one-another when they are twisted.

DESCRIPTION OF THE DRAWINGS

In the following the invention will be further described with references to the drawings, wherein.

In the figures like structures are generally identified by like reference numerals.

POSITION NUMBERS OF THE DRAWINGS

Figure 1:
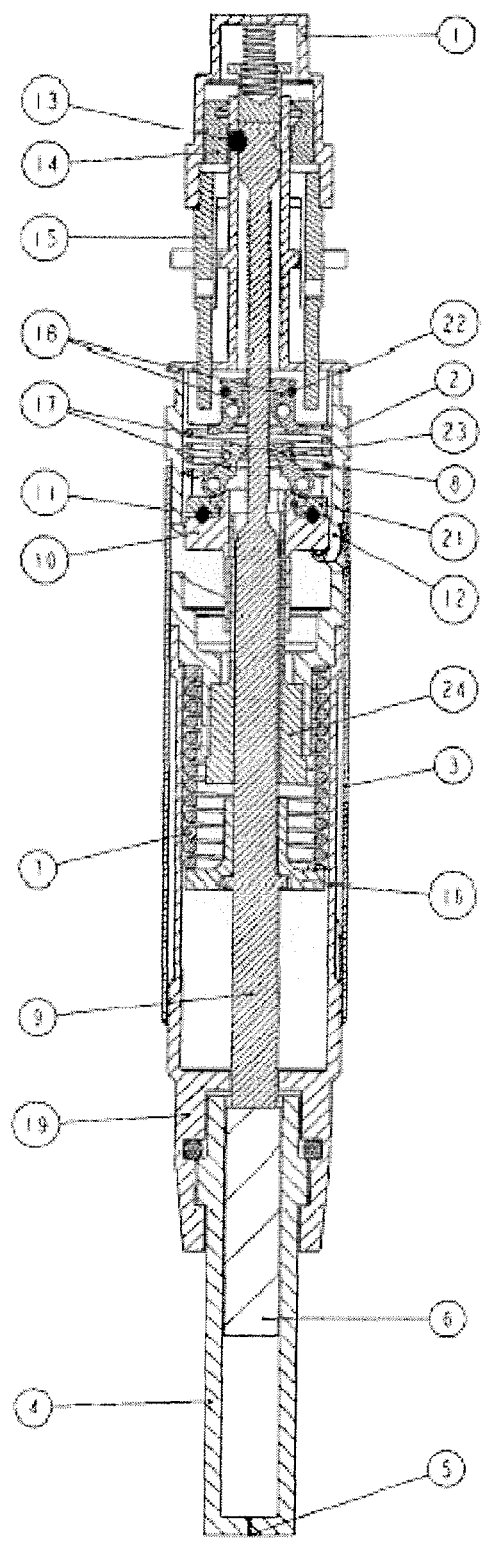
FIG. 1 shows a pressurized injection device according to the invention in its loaded state in sectional view.
Figure 2:
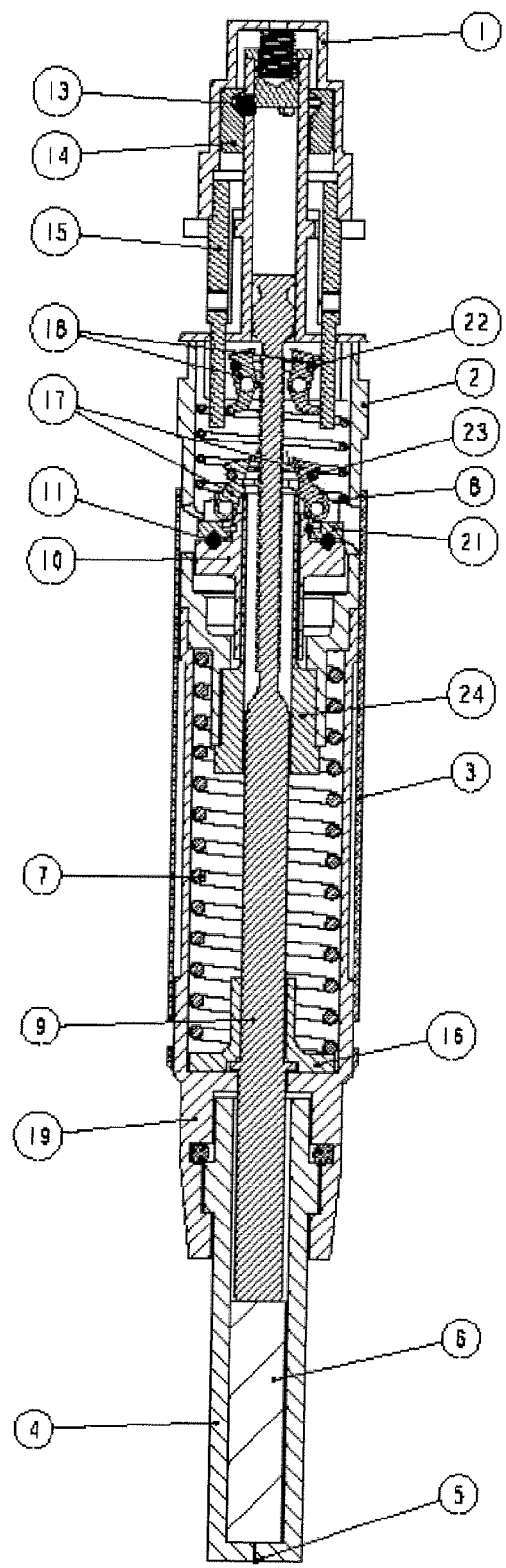
FIG. 2 shows a pressurized injection device according to the invention in its let off state in sectional view.

1. Button
2: Curved track member
3: Shell
4: Container
5: Orifice/(needle)
6: Piston
7: Spring
8: Ratchet return spring
9: Piston rod
10: Lower carrier
11: Balls
12: Rolling member
13: Balls/rollers
14: Locking member
15: Release member
16: Hollow part
17: Ratchet arm
18: Ratchet arm
19: Lower body
20: Curved track
21: Ratchet arm holder
22: Upper ratchet arms
23: Stopper member
24: Ratchet release member

DESCRIPTION OF EXEMPLARY EMBODIMENTS

When in the following terms as "distal", "proximal" and "radial" or similar relative expressions are used, these only refer to the appended figures and not necessarily to an actual situation of use. The shown figures are schematic representations for which reason the configuration of the different structures as well as there relative dimensions are intended to serve illustrative purposes only.

Figure 3:
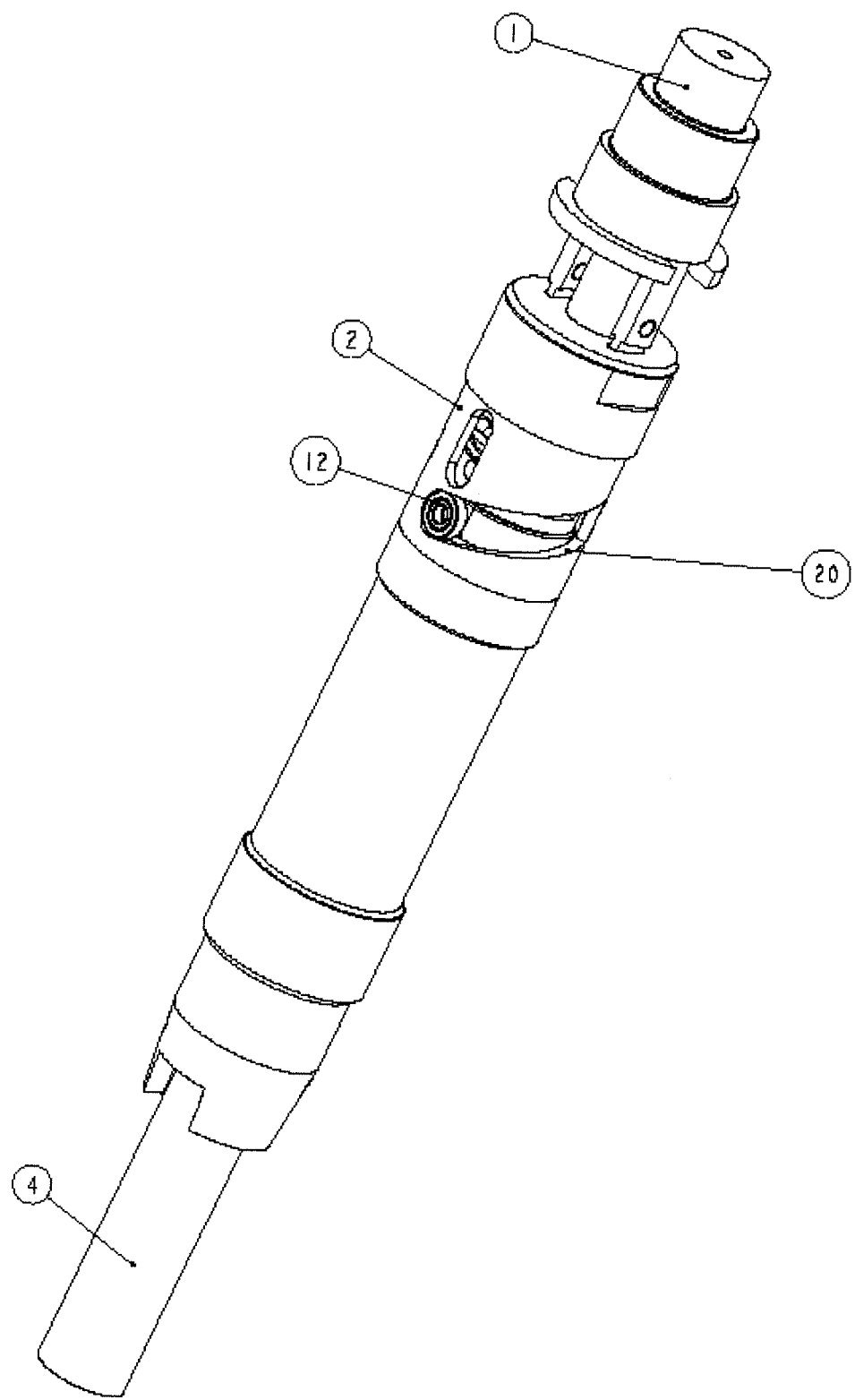
FIG. 3 shows a pressurized injection device according to the invention seen from the outside showing the curved track.

FIG. 1 depicts the mechanism with the resilient element in a loaded state, where the resilient element is pre-stressed. The basic idea of this mechanism is to load a resilient element, in this example a mechanical spring, in a number of twists provided by the user. The force of the spring is hereafter used to deliver an impulse to an injection unit, in this example a jet injection unit, whereby a liquid volume is pressurised so it can exit either through an orifice (or a needle). The container 4 holds a liquid volume enclosed by a piston 6 and an outlet orifice (alternatively needle) 5 which allows pressurised liquid to exit the container. A piston rod 9 acts on the piston and has a ladder rack at which 2 sets of ratchet arms 17 & 18 engages. At the bottom a hollow part 16 attaches to an axle collar at the piston rod which carries the load of the operating spring 7. When the spring 7 is loaded, the outer shell is rotated which forces the ball bearing (alternatively a sliding axle journal) to follow the curved track 20 (FIG. 3) since the axle of the ball bearing is attached to both the lower carrier 10 and the shell 3. The curved movement of the lower carrier causes it to lift the ratchet arm holder 21 in a vertical direction through a number of balls 11 rolling in the curved track. The lower ratchets 17 of the ratchet arm holder are embedded in the holder 21 by a set of axles allowing them to rotate in the plane of the figure. These ratchets have an O-ring shaped elastic member securing engagement of the ratchet arms 17 in the teeth of the ladder rack of the piston rod 9. When the shell 3 has been turned to the end of the curved track 20 it is reversed back to the original position. In the beginning of this reversing movement, the upper ratchet arms 18 that are embedded in the curved track member 2, engages with teeth of the of the ladder rack. This engagement prevents the downward movement of the piston rod 9 while the lower carrier 10 is lowered during the reverse operation. The twisting of the outer shell is repeated back and forth in a cyclic movement, until the top groove of the piston rod 9 engages a set of balls or rollers 13 forced in position by a locking member 14. When the shell 3 is reversed after this locking of the piston rod 9, the stopper member 23 disengages the lower set of ratchet arms 17 with the piston rod 9.

The mechanism is now in its loaded state. The liquid dispersion is initiated by pushing the button 1 downwards which will bring along the locking member 14 and the release member 15. First, the release member 15 will act on the upper ratchet arms 22 which will disengage from the piston rod 9. Right hereafter the locking member 14 will allow the balls/rollers 13 to translate outwards driven by the force of the spring 7. The force of the spring 7 will cause the liquid dispersion from the container 4 as it pushes the piston 6 downwards.

FEATURES OF THE INVENTION

1. A medical device comprising;
A resilient element for storing and delivering a force profile to an injection unit, said resilient element is pre-stressed by a loading mechanism, said loading mechanism is adapted to translate a cyclic rotational relative movement between a first part and a second part of said medical device into a linear compression of said resilient element characterized in that, the medical device further comprises at least one low friction force transfer element(s) controlling the force transfer between said first and second part of the medical device.

2. A medical device according to clause 1, characterized in that said low friction force transfer element(s) comprises one or more ball bearing(s), roller bearing(s), slide bearing(s), ball and guide bearing(s), roller and guide bearing(s) or linked joint(s)

3. A medical device according to any of the clauses 1 or 2, characterized in that, said first part, or said second part or both first and second part of said medical device comprise(s) one or more curved track(s) or guide(s), or track(s) or guide(s) angled to the perpendicular of the centre line of said device, said track(s) or guide(s) being adapted to cooperate with said force transfer element(s) when the first and the second part of said medical device are rotated relative to one another.

4. A medical device according to any of the preceding clauses, characterized in that, said medical device comprises at least one first and at least one second one-way fixation means, the first one-way fixation means prevents relative axial movement between the first part of the medical device and a load carrier (16) of the resilient element when the first part and the second part of the medical device are relatively rotated in a first direction, whereby the resilient element is compressed; and the second one-way fixation means prevents relative axial movement between the second part of the medical device and said load carrier (16) when the first part and the second part of the medical device are relatively rotated in a second direction whereby the two parts of the medical device are reversed, and whereby the resilient element is pre-stressed in steps without the user needing to change grip of the medical device.

5. A medical device according to clause 4, characterized in that, said one-way fixation means comprises one or more ratchet(s), one or more wedge(s) or one or more wedge and roller(s).

6. A medical device according to any of the preceding clauses, characterized in that, the resilient element is a spring.

7. A medical device according to any of the preceding clauses, characterized in that, said medical device is a medical jet injection device.

The invention claimed is:

1. A medical device comprising;
a resilient element for storing and delivering a force profile to an injection unit, said resilient element is pre-stressed by a loading mechanism, said loading mechanism is adapted to translate a reciprocating rotational relative movement between a first part and a second part of said medical device into a linear compression of said resilient element,
wherein the medical device further comprises at least one low friction force transfer element(s) controlling the force transfer between said first and second part of the medical device.

2. A medical device according to claim 1, wherein said low friction force transfer element(s) comprises one or more ball bearing(s), roller bearing(s), slide bearing(s), ball and guide bearing(s), roller and guide bearing(s) or linked joint(s).

3. A medical device according to any of the claim 1, wherein, said first part, or said second part or both first and second part of said medical device comprise(s) one or more curved track(s) or guide(s), or track(s) or guide(s) angled to the perpendicular of the centre line of said device, said track(s) or guide(s) being adapted to cooperate with said force transfer element(s) when the first and the second part of said medical device are rotated relative to one another.

4. A medical device according to claim 1, wherein said medical device comprises at least one first and at least one second one-way fixation means, the first one-way fixation means prevents relative axial movement between the first part of the medical device and a load carrier (16) of the resilient element when the first part and the second part of the medical device are relatively rotated in a first direction, whereby the resilient element is compressed; and the second one-way fixation means prevents relative axial movement between the second part of the medical device and said load carrier (16) when the first part and the second part of the medical device are relatively rotated in a second direction whereby the two parts of the medical device are reversed, and whereby the resilient element is pre-stressed in steps without the user needing to change grip of the medical device.

5. A medical device according to claim 4, wherein said one-way fixation means comprises one or more ratchet(s), one or more wedge(s) or one or more wedge and roller(s).

6. A medical device according to claim 1, wherein the resilient element is a spring.

7. A medical device according claim 1, wherein said medical device is a medical jet injection device.

* * * * *